(12) United States Patent
Bakkene et al.

(10) Patent No.: US 7,824,728 B2
(45) Date of Patent: Nov. 2, 2010

(54) WHEY PROTEIN AND LIPID COMPOSITION

(75) Inventors: Gunnar Bakkene, Kleppe (NO); Berit Nordvi, Tårnåsen (NO); Anne-Grethe Johansen, Halden (NO); Miguel A. Gutierrez, Bergen (NO)

(73) Assignee: Tine BA, Oslo (NO)

( * ) Notice: Subject to any disclaimer, the term of this patent is extended or adjusted under 35 U.S.C. 154(b) by 1303 days.

(21) Appl. No.: 11/293,506

(22) Filed: Dec. 5, 2005

(65) Prior Publication Data

US 2007/0128341 A1 Jun. 7, 2007

(30) Foreign Application Priority Data

Dec. 1, 2005 (NO) .................. 20055686

(51) Int. Cl.
*A23J 1/04* (2006.01)
(52) U.S. Cl. ............... 426/657; 426/569; 426/583; 426/586; 426/588; 426/591; 426/594; 426/596; 426/471; 426/443
(58) Field of Classification Search ........... 426/657, 426/569, 583, 586, 588, 591, 594, 596, 471, 426/443
See application file for complete search history.

(56) References Cited

U.S. PATENT DOCUMENTS 6,168,819 B1 * 1/2001 Zeller et al. .......... 426/569
6,824,810 B2 11/2004 Sargent et al. ........... 426/588

FOREIGN PATENT DOCUMENTS

| WO | WO 89/05587 | 6/1989 |
| WO | WO 91/17665 | 11/1991 |
| WO | WO 94/01001 | 1/1994 |
| WO | WO 03/090560 | 11/2003 |

OTHER PUBLICATIONS

Levy et al. The Influence of Temperature and pH Upon the Rate of Deanturation of Ricin. 1950.*
de la Fuente et al., "Recent Advances in the Characterisation of Heat-Induced Aggregates and Intermediates of Whey Proteins," Trends in Food Science & Technology 13:262-74 (2002).
Cheftel et al., "Amino Acids, Peptides, and Proteins," Food Chemistry, pp. 279-282 (O.R. Fennema eds., Marcel Dekker, Inc., 2nd ed. 1985).

* cited by examiner

*Primary Examiner*—Anthony Weier
(74) *Attorney, Agent, or Firm*—Fitzpatrick, Cella, Harper & Scinto

(57) ABSTRACT

The present invention relates to liquid and powdered compositions as well as emulsions comprising whey protein and lipid, particularly fish oil, suitable for enrichment of a variety of food articles and beverages with poly unsaturated fatty acids like omega-3 fatty acids. The composition may also be consumed as such. Furthermore, the present invention relates to a process of preparing such compositions and emulsions. The main feature of the process of the present invention, is that the microencapsulation of the lipid is made simultaneously with the microparticulation of the protein. A composition having superior properties in terms of taste and stability, is provided by the present invention.

18 Claims, No Drawings

WHEY PROTEIN AND LIPID COMPOSITION

FIELD OF THE INVENTION

The present invention relates to liquid and powdered compositions as well as emulsions comprising whey protein and lipid, particularly fish oil, suitable for enrichment of a variety of food articles and beverages with for instance polyunsaturated fatty acids like omega-3 fatty acids. The composition may also be consumed as such. Furthermore, the present invention relates to a process of preparing such compositions and emulsions.

In the following, the terms "emulsion(s)" and "powder(s)" will sometimes be used. However, these terms should herein be considered as encompassing the term "liquid and powdered composition(s)". Furthermore, the term "composition(s)" used herein alone, should be considered as encompassing the term "liquid and powdered compositions as well as emulsions".

The term "lipid" or "lipid component" as used herein encompasses oils, fats, fatty acids or derivatives of fatty acids like esters and triglycerides.

BACKGROUND OF THE INVENTION

The consumption of certain polyunsaturated fatty acids (PUFAs), mainly through food or beverage compositions is beneficial for diverse health concerns. The strong scientific evidence on the health benefits of omega-3 fatty acids is supported by more than 6.000 published studies. They suggest that diets rich in omega-3 very long chain polyunsaturated fatty acids (EPA and DHA) help maintaining the performance of the heart and the cardiovascular system by reducing the levels of triglycerides (fats) in the blood, by supporting the blood pressure regulation and maintaining a regular heartbeat. In addition, omega-3 polyunsaturated fatty acids have demonstrated their beneficial effects on the maintenance of healthy bones and joints particularly due to prevention of inflammation. Mounting evidence also suggests that omega-3 PUFAs have positive effects on schizophrenia, depression, Alzheimer's disease, neurodevelopmental and other psychic disorders. Omega-3 polyunsaturated fatty acids also play an important role during pregnancy and in infant development.

Omega-3 and omega-6 PUFAs are considered essential to health, and are thus when used as ingredients of functional foods, providing a multitude of benefits unmatched by other food ingredient.

Nutrition in the Western Hemisphere is by some scientists considered to have an imbalance of omega-3 and omega-6 fatty acids, with too high proportion of omega-6 fatty acids. It is therefore recommended by many to increase the intake of omega-3 fatty acids.

Food fortification with PUFAs, and in particular long-chain omega-3 fatty acids, is therefore highly desirable. However, despite large efforts made from the oil and food industries, it is still a challenge to prepare palatable food and beverage products due to oxidative deterioration of the omega-3 fatty acids and the sources thereof leading to off-flavour formation and poor storage stability.

A good initial quality with a clean sensory profile of the source of PUFAs is a key aspect in this kind of food fortification. The most common sources of long-chain omega-3 fatty acids are fish oils (DHA and EPA) from various sources including salmon, cod, menhaden and tuna eye socket, as well as algae sources (DHA). Other marine and plant oils and fats are sources of PUFAs as well.

Lipid oxidation rendering to rancidity is a problem connected to fish oil and fish fat-rich products during storage and processing.

Unpleasant side effects of ingesting fish oil supplements like halitosis, eructation and "fishy" smelling breath, skin and even urine have been reported. Objectionable fishy off-flavours due to volatile fish oil oxidation products is thus an obstacle in the development of fish oil enriched foods and beverages.

It is a major challenge for the food industry to overcome the undesirable side effects typically associated with the use of PUFA ingredients, such as strong fishy flavours and aromas.

Moreover, whey protein has well documented nutritional advantages. Whey has the highest biological value of all proteins, it contains all essential amino acids, which are vital for human metabolism, and to make human body function properly for good health. Whey also boasts the highest concentrations of branched chain amino acids (BCAA's) found in nature. BCAA's are an important source of energy during exercise and play a key role in protein synthesis. This makes whey the most popular protein for athletes and sport people.

Encapsulation of the fish oil is one of the most promising methods to prevent oxidation and therefore, rancidity of foods containing fish oil.

Furthermore, the high degree of susceptibility of such omega-3 oils makes a case for microencapsulation in a matrix that makes them suitable for food applications. For instance as disclosed in International patent application WO 9401001, which relates to microencapsulation of an oil or fat having a content of at least 10% highly unsaturated fatty acid by homogenising a mixture of the oil and an aqueous solution of a caseinate at a pressure above 200 bar. The resulting emulsion is then dried by using methods known per se to obtain free flowing microcapsules.

Besides stabilising these omega-3 oils, microencapsulation provides compositions that may be favourable to include in various food products also for other reasons such as convenience of addition; product compatibility; protection from secondary thermal processes like baking and extrusion; prevention of ingredient interactions (as, for example, DHA interacts negatively with certain artificial colours and flavours); and, above all, to extend shelf life of the fortified food.

Among the numerous processes known for producing microencapsulated oil, proteins from plant, egg or milk, including whey, are involved as microencapsulating agents.

US patent application having publication no. 2004/0062846, relates to creamer compositions and methods of making and using the same. These compositions comprise a primary (microparticulated) and a secondary ingredient component. The primary microparticulated ingredient component comprises 0.1-80% of a fat/oil component, and 0.1-70% of a microparticulated protein component. The secondary ingredient comprises an emulsifier and a bulking agent. The protein sources mentioned are plant proteins, dairy proteins, animal proteins and mixtures thereof. The process of preparing the creamer composition requires heating of the oil/fat until liquefaction, then addition of water and agitation, and furthermore addition of protein which is already microparticulated and then a two step homogenization firstly at 30 to 100 bar, and secondly at 100 to 300 bar. The obtained composition should be subjected to one or more sterilization processes to render microbiological stability. This process is rather cumbersome and expensive due to the large number of different steps and many essential ingredients.

In International patent application WO 03/090560, compositions of protein and fatty acid useful as food or beverage compositions are disclosed. The compositions are prepared by combining the protein component with the lipid component to form a protein/lipid mixture, and subjecting this mixture to a condition selected from the group consisting of: (a) high shear conditions, (b) homogenization, and combinations thereof. Microparticulation is not mentioned. In the said process addition of emulsifiers and minerals are preferred in order to avoid rupture of the oil vesicles during homogenization.

It is now surprisingly found that by microparticulating a whey protein component and a lipid component simultaneously, a composition of high concentration of fatty acid material, which is stable, pasteurized, organoleptically appealing with long shelf life and thereby useful for a variety of purposes, especially as ingredient to foods and beverages, is obtained. The said composition is capable of being subjected to UHT (ultra high temperature) treatment if necessary. Moreover, the composition obtained has a high content of whey protein which is very desirable for athletes and sports people.

SUMMARY OF THE INVENTION

It is a main object of the present invention to provide a simple method for producing a composition of lipid and protein wherein different kinds of additional additives like carbohydrates, emulsifiers, bulking agents, antioxidants, etc. are not required.

Another object of the present invention is to provide a composition of lipid and protein that is organoleptically appealing as such, and when added to foods or beverages.

Another object of the present invention is to provide a composition of lipid and protein having an acceptable storage stability; that is stable in terms of taste, smell, oxidation and microbial growth; and in terms of separation and viscosity (i.e. physical stability).

These and other objects are obtained by the composition, process and uses as defined in the accompanying claims.

In particular, the present invention provides a composition comprising:
a) a protein component consisting of whey protein concentrate in liquid and/or powdered form and/or concentrate of whey and/or non-concentrated whey and/or a mixture thereof, and other proteins;
wherein the source of the protein component comprises non-denatured whey protein in a concentration of no less than 40% of the total concentration of protein, and
wherein the concentration of any of the said other proteins is below 40% of the total concentration of protein, and
wherein the denaturation rate of the individual whey proteins in the composition is from 50% to 99%; and
b) a lipid component not originating from the said protein component.

Furthermore, the present invention provides a process for preparing a composition as defined above, comprising:
a) mixing,
a protein component consisting of whey protein concentrate in liquid and/or powdered form and/or concentrate of whey and/or non-concentrated whey and/or a mixture thereof, and other proteins, wherein the source of the protein component comprises non-denatured whey protein in a concentration of no less than 40% of the total concentration of protein, and wherein the concentration of any of the said other proteins is below 40% of the total concentration of protein, and a lipid component not originating from the said protein component, according to a food processing method known in the art, to make a homogenous mixture;
b) heating the said mixture to 60-70° C. under mild agitation,
c) bringing the mixture from step b) to a shear rate of >400 per sec. in one or more scraped surface heat exchanger(s) (SSHE) constituting a heating section wherein the temperature is from 72-11° C., and
d) after a holding time of 1-10 min.,
e) bringing the mixture from step d) to a shear rate of >400 per sec. in further one or more SSHE(s) constituting a cooling section to obtain the composition having a temperature below the denaturation temperature of whey protein when leaving the cooling section.

The present invention also provides the use of a composition as defined above as such or as ingredients in foods and beverages, health foods, nutritions for special dietetic purposes, infant formulas, pharmaceuticals and feeds.

Foods comprises fermented milk based products such as yoghurt, quark, cheeses, cream cheeses, sour cream, butter, margarines, spreads, dressings and ricotta; processed fish and meat products such as fish cakes, fish puddings, rissoles, hamburgers, meat loafs and pâtés; soups and sauces; breads, bakery's, cakes, biscuits, flour mixtures and cereals; energy bars, cake fillings, chocolates and confectionary candies. Health foods and food supplements are also included.

Beverages comprises milk, drinking yoghurt, flavoured drinks, juices and nectars based on fruits, berries and/or vegetables, smoothies, fermented milk based drinks and other fermented drinks, other milk or fruit based drinks, soft drinks, sports drinks, water based drinks and functional food drinks.

DETAILED DESCRIPTION OF THE INVENTION

The protein component of the invention consists of whey protein concentrate in liquid and/or powdered form and/or concentrate of whey and/or non-concentrated whey and/or a mixture thereof, and other proteins.

The term "whey protein concentrate in liquid and/or powdered form" as used herein includes whey protein isolate as well as whey protein retentate.

The protein component used as a starting material for preparing the composition according to the present invention comprises non-denatured whey protein in a concentration of no less than 40% of the total concentration of protein. Preferably, the source of the protein component comprises non-denatured whey protein in a concentration no less than 50% of the total concentration of protein. More preferred the said concentration of non-denatured whey protein is no less than 60%, 70%, 75%, 80%, 85%, 90%, and most preferred no less than 95%.

The source of whey protein can be non-concentrated whey and whey concentrate and/or concentrate of whey protein from 20% to 90% of whey protein in dry matter (WPC-20-WPC-90), and/or whey protein isolate and/or a mixture thereof. Non-concentrated whey may not be a part of the whey protein source. The protein component may be in liquid or powdered form.

Furthermore the concentration of any of the said other proteins in the composition is below 40% of the total concentration of protein.

When other proteins are used, these can be selected from the group consisting of casein and its caseinates (e.g. sodium caseinate, calcium caseinate), milk based powders, butter milk powder and/or plant, vegetable and/or marine proteins, egg proteins or other animal proteins as well as microbial proteins, or its hydrolysates, in liquid and/or in powdered form.

The amount of protein component in the compositions when present in liquid form, comprises from about 1% to 30% of protein, more preferable from 3% to 25% and even more preferable from 6% to 20%. All by weight of the composition.

In the composition of the present invention the denaturation rate of the individual whey proteins is from 50% to 99%. Preferably, the denaturation rate of the individual whey proteins is above 70%, more preferable the denaturation rate of the individual whey proteins is above 80%, and most preferable the denaturation rate of the individual whey proteins is above 90%.

The lipid component employed in the composition of the present invention includes any edible oil or fat. The oils or fats may comprise saturated, partially saturated, unsaturated fatty acids and/or derivatives thereof and/or mixtures thereof. Preferably the oils or fats comprise a high content of polyunsaturated fatty acids or derivatives thereof.

Such edible oils and fats are derived from plant, animal, marine or microorganism sources. Plant sources include soybean oil, canola oil, corn oil, cottonseed oil, peanut oil, safflower oil, sunflower oil, rapeseed oil, sesame seed oil, olive oil, coconut oil, palm kernel oil, and palm oil. Oils and fats from a genetically modified organism (GMO) are included.

Microorganism sources include single cell organisms.

Animal sources include tallow, butter, lard, and egg yolk oil.

Oils from marine sources (e.g. fish oil, like cod, menhaden, tuna, herring, sand eel, sprat, anchovy, capelin, sardine, salmon, trout or mackerel oil; fish liver oil, like cod, halibut or shark liver oil; krill oil; whale oil; seal oil), including algae sources, and mixtures thereof, are preferred.

The amount of lipid component in the compositions may amount to as much as 70%.

Preferably, the amount of lipid in the composition is from about 1% to 30%, more preferable 10% to 25%, and even more preferable, from 12 to 25% by weight of the composition when present in liquid form or powdered form thereof.

The ratio of protein to fat in the composition of the present invention ranges from 0.3 to 30.0, more preferable 0.3 to 10.0, and most preferable from 0.3 to 4.0.

The median particle size in the composition according to the invention is about 1 micron, and the median particle size distribution ranges from 0.1 micron to 50 micron more preferable from 0.4 micron to 10 micron.

The compositions of the present invention have the particularity of comprising only a protein and lipid component as essential components. No addition of further ingredients/materials like emulsifiers, carbohydrates, salts, bulking agents, minerals, flavouring agents etc. is necessary to enhance stability or organleptic properties of the emulsion or powder. In the case of antioxidants, the only ones used are those to preserve the oil before it is used in the emulsion or the powder. After the emulsion is manufactured, no addition of antioxidants is necessary. However, if desired, the mentioned further ingredients as well as antioxidants can be added without deterioration of the emulsion properties.

The main feature of the process of the present invention, is that the microencapsulation of the oil is made simultaneously with the microparticulation of the protein.

The process comprises preparing a composition as defined above, wherein the protein and lipid components firstly are mixed according to a food processing method known in the art, to make a homogenous mixture.

The said mixture is then subjected to microparticulation of the protein component which also result in microencapsulation of the lipid by bringing the said mixture, that is heated to 60-70° C. under mild agitation, to a shear rate of >400 per sec. in one or more scraped surface heat exchanger(s) (SSHE) constituting a heating section wherein the temperature is from 72-110° C., and after a holding time of 1-10 min. at this temperature, bringing the mixture further on to a shear rate of >400 per sec. in further one or more SSHE(s) constituting a cooling section to obtain the composition having a temperature below the denaturation temperature of whey when leaving cooling section.

Further cooling of the composition obtained to about 4° C. may be performed if desired.

In another embodiment of the invention the composition obtained may immediately be subjected to ultra high temperature (UHT) treatment.

The temperature in the heating section is preferably from 80-105° C., more preferable from 85-105° C., and most preferable from 90-105° C.

The shear rate in the SSHEs is preferably above 600 per sec, and more preferred from 600-800 per sec.

The holding time of the mixture between the heating section and the cooling section is a time long enough to reach a denaturation rate of the individual whey proteins from 50% to 99%; i.e. 1-10 minutes.

The temperature of the composition when leaving the cooling section is preferably below 75° C., more preferred below 50° C.

In a preferred embodiment of the present invention, the mixture pre-treated according to a previously known food processing method is subjected to simultaneous microparticulation of the protein component and microencapsulation of the lipid, by:

i) heating to 60-70° C. and subjecting to mild stirring;
ii) transferring to a first SSHE wherein the temperature is 72-100° C. and the shear rate is above 600 per sec., and after maintenance of this temperature and share rate for 1-5 min.;
iii) transferring to a second SSHE wherein the shear rate is equal to the shear rate in the first SSHE to cooling the composition obtained to below 75° C.

The present invention provides a unique process for achieving a pasteurized composition with denaturation rate of the individual whey proteins from 50% to 99%. Further pasteurization will not be necessary to perform for the obtained compositions. In order to increase the storage stability of the composition, UHT treatment may easily be performed without any functional changes in the composition. In addition, the achievement of the high protein denaturation rate in presence of oil produces remarkable microencapsulation properties that enable a stable composition, capable of resisting further pH adjustments without the need of additional emulsifiers.

The pH in the mixtures that are subjected to simultaneously microparticulation and microencapsulation according to the present invention may vary, which will results in compositions with different pH.

The compositions of the invention are organoleptically outstanding wherein the median particle size distribution ranges from 0.1 micron to 50 micron, more preferable 0.4 micron to 10 micron.

The composition in liquid/emulsion form may be de-watered by spray drying, freeze drying or fluid bed drying to form a powder without need for addition of any bulking and/or drying agents.

However, if desired, emulsifiers, carbohydrates, salts, antioxidants, flavouring agents, bulking agents and/or drying agents may be added to the emulsion before drying.

The simultaneous process of the invention produces an emulsion or powder that does not require addition of any additional ingredient components. Whey and lipid are the only required ingredients.

The emulsion or powder can be use to enrich with for instance Omega 3 oil any kind of food products or beverages. Healthy functional foods, dietetic foods and pharmaceuticals where a high content of oil containing polyunsaturated fatty acids is desired, are also obtainable by addition of the compositions of the present invention. The composition of the present invention may as well be consumed as such in form of an emulsion, drink or powder.

In addition to the health benefits of the lipid, the whey protein matrix of the invention is in itself a natural nutrient which does not contain any additives and protects the oil against oxidative degradation.

The high content of whey protein provided in the compositions of the invention makes the compositions relevant as protein supplements for athletes and sport people.

A composition comprising a high amount of omega-3 PUFA having superior properties in terms of taste and stability, is provided by the present invention.

The invention is explained in more detail in the examples below.

EXAMPLE 1

To demonstrate the superior properties of a composition of the present invention, several analyses were performed of a sample of a composition prepared according to the process of the present invention. Similar analyses of compositions prepared according to methods known from the prior art were performed as well for the purpose of comparison.

Preparation of a Composition of the Present Invention

Emulsion

A mixture of non-denatured whey protein having a whey protein concentration of 60% in total solids (WPC 60) and 2% sodium caseinate of the composition, in a protein concentration of 20% in the water phase of the composition, and 20% fish oil was prepared according to a conventional food processing method. The mixture was then transferred to a SSHE and subjected to a shear rate >600 per sec. and a temperature from 85-95° C. for 1-5 min. After further treatment at the same shear rate and a temperature of <75° C. in a second SSHE, an emulsion was obtained.

Powder

The emulsion prepared above, was dried by conventional spray drying.

Preparation of Comparison Compositions A1 and A2

A mixture of non-denatured whey protein having a whey protein concentration of 60% of total solids (WPC 60) and 2% sodium caseinate of the composition, in a protein concentration of 20% in the water phase of the composition, and 20% fish oil was prepared according to a conventional food processing method and subjected to homogenisation at two different conditions to form two different emulsions, A1, A2.
A1: The homogenisation was performed once at 150 bar.
A2: The homogenisation was performed three times at 150 bar.

A third emulsion (A3) processed by homogenisation at 500 bar was not possible to obtain, as the viscosity of the emulsion was too high for this kind of equipment.

By conventional spray drying, emulsions A1 and A2 were formed to powders. Due to high viscosity of the emulsions, large amounts of water had to be added to the composition to enable spray drying.

Preparation of Comparison Compositions B1, B2 and B3

Non-denatured whey protein having a whey protein concentration of 60% of total solids (WPC 60) and 2% sodium caseinate of the composition, in a protein concentration of 20% in the water phase of the composition was subjected to a conventional food processing method. This aqueous mixture was microparticulated according to a previously known technique. 20% fish oil was added to the microparticulated proteins, and this mixture was then homogenized under three different conditions to obtain three different emulsions, B1, B2, B3.
B1: The homogenisation was performed once at 150 bar.
B2: The homogenisation was performed three times at 150 bar.
B3: The homogenisation was performed once at 500 bar.

Production of B3 was only possible after addition of large amount of water to the composition, and after heating of the composition to approx. 60-70° C. prior to processing. Without this pre-treatment, the viscosity of the composition increased too much to be processed by this method.

By conventional spray drying, emulsions B1, B2 and B3 were formed to powders. Similar to compositions A1 and A2, the viscosity of the emulsions B1-B3 were high, and large amounts of water had to be added to enable spray drying.

Analyses

The emulsions and powders performed were tested with regard to storage stability with regard to oxidation stability and physical properties, such as: taste, particle size distribution, rheological parameters, turbiscan and centrifugation stability, protein/fat ratio, degree of protein denaturation and solubility. The emulsion and powder according to the invention showed better results in all the tests performed compared to emulsions A1, A2, B1, B2 and B3, and the powders thereof.

The emulsion according to the invention had a remarkably low viscosity, high physical stability, and good smell and taste without unwanted fishy off-favour. It was furthermore found that the emulsion had a very high physical stablity, low viscosity and a good and acceptable taste during a long storage period of more than 4 months.

Due to the low viscosity of the emulsion of the invention, the spray drying process could be done by use of a more concentrated solution than what was the case for the emulsions of the comparative examples. This resulted in a much better production economy for the powder of the invention.

The powder according to the invention had a good and acceptable taste (i.e. no fishy off-flavour) and good storage stability for more than 4 months.

EXAMPLE 2

A composition of the present invention was prepared as follows:

A mixture of non-denatured whey protein having a whey protein concentration of 60% of total solids (WPC 60) and 2% sodium caseinate of the composition, in a protein concentration of 10% in the water phase of the composition, and 10% fish oil was prepared according to a conventional food processing method. The mixture was then transferred to a SSHE and subjected to a shear rate >600 per sec. and a temperature of 85° C. for 1-5 min. After further treatment at the same shear rate and a temperature of <75° C. in a second SSHE, the composition obtained was subjected to spray drying and a powder was achieved.

The composition (emulsion) provided, was tested both for physical stability and organoleptic properties and gave good scores in these tests.

EXAMPLE 3

A composition of the present invention was prepared as follows:

A mixture of non-denatured whey protein having a whey protein concentration of 60% of total solids (WPC 60) and 2% sodium caseinate of the composition, in a protein concentration of 10% in the water phase of the composition, and 10% fish oil was prepared according to a conventional food processing method. The mixture was then transferred to a SSHE and subjected to a shear rate >600 per sec. and a temperature of 95° C. for 1-5 min. After further treatment at the same shear rate and a temperature of <75° C. in a second SSHE, the composition obtained was subjected to spray drying and a powder was achieved.

The composition (emulsion) provided, was tested both for physical stability and organoleptic properties and gave good scores in these tests.

EXAMPLE 4

A composition of the present invention was prepared as follows:

A mixture of non-denatured whey protein having a whey protein concentration of 60% of total solids (WPC 60) and 2% sodium caseinate of the composition, in a protein concentration of 10% in the water phase of the composition, and 25% fish oil was prepared according to a conventional food processing method. The mixture was then transferred to a SSHE and subjected to a shear rate >600 per sec. and a temperature of 85° C. for 1-5 min. After further treatment at the same shear rate and a temperature of <75° C. in a second SSHE, an emulsion was obtained.

The emulsion provided, was tested both for physical stability and organoleptic properties and gave good scores in these tests.

EXAMPLE 5

A composition of the present invention was prepared as follows:

A mixture of non-denatured whey protein having a whey protein concentration of 60% of total solids (WPC 60) and 2% sodium caseinate of the composition, in a protein concentration of 10% in the water phase of the composition, and 25% fish oil was prepared according to a conventional food processing method. The mixture was then transferred to a SSHE and subjected to a shear rate >600 per sec. and a temperature of 95° C. for 1-5 min. After further treatment at the same shear rate and a temperature of <75° C. in a second SSHE, an emulsion was obtained.

The emulsion provided, was tested both for physical stability and organoleptic properties and gave good scores in these tests.

EXAMPLE 6

A composition of the present invention was prepared as follows:

A mixture of non-denatured whey protein having a whey protein concentration of 60% of total solids (WPC 60) and 2% sodium caseinate of the composition, in a protein concentration of 20% in the water phase of the composition, and 10% fish oil was prepared according to a conventional food processing method. The mixture was then transferred to a SSHE and subjected to a shear rate >600 per sec. and a temperature of 85° C. for 1-5 min. After further treatment at the same shear rate and a temperature of <75° C. in a second SSHE, an emulsion was obtained.

The emulsion provided, was tested both for physical stability and organoleptic properties and gave good scores in these tests.

EXAMPLE 7

A composition of the present invention was prepared as follows:

A mixture of non-denatured whey protein having a whey protein concentration of 60% of total solids (WPC 60) and 2% sodium caseinate of the composition, in a protein concentration of 20% in the water phase of the composition, and 10% fish oil was prepared according to a conventional food processing method. The mixture was then transferred to a SSHE and subjected to a shear rate >600 per sec. and a temperature of is 95° C. for 1-5 min. After further treatment at the same shear rate and a temperature of <75° C. in a second SSHE, an emulsion was obtained.

The emulsion provided, was tested both for physical stability and organoleptic properties and gave good scores in these tests.

EXAMPLE 8

A composition of the present invention was prepared as follows:

A mixture of non-denatured whey protein having a whey protein concentration of 80% of total solids (WPC 80) and 2% soy protein of the composition, in a protein concentration of 15% in the water phase of the composition, and 15% fish oil was prepared according to a conventional food processing method. The mixture was then transferred to a SSHE and subjected to a shear rate >600 per sec. and a temperature of 85° C. for 1-5 min. After further treatment at the same shear rate and a temperature of <75° C. in a second SSHE, an emulsion was obtained.

The emulsion provided, was tested both for physical stability and organoleptic properties and gave good scores in these tests.

EXAMPLE 9

A composition of the present invention was prepared as follows:

A mixture of non-denatured whey protein having a whey protein concentration of 80% of total solids (WPC 80) and 2% soy protein of the composition, in a protein concentration of 15% in the water phase of the composition, and 15% fish oil was prepared according to a conventional food processing method. The mixture was then transferred to a SSHE and subjected to a shear rate >600 per sec. and a temperature of 95° C. for 1-5 min. After further treatment at the same shear rate and a temperature of <75° C. in a second SSHE, an emulsion was obtained.

The emulsion provided, was tested both for physical stability and organoleptic properties and gave good scores in these tests.

EXAMPLE 10

A composition of the present invention was prepared as follows:

A mixture of non-denatured whey protein having a whey protein concentration of 80% of total solids (WPC 80) and 2% sodium caseinate of the composition, in a protein concentration of 15% in the water phase of the composition, and 25% fish oil was prepared according to a conventional food processing method. The mixture was then transferred to a SSHE and subjected to a shear rate >600 per sec. and a temperature of 85° C. 1-5 min. After further treatment at the same shear rate and a temperature of <75° C. in a second SSHE, an emulsion was obtained.

The emulsion provided, was tested both for physical stability and organoleptic properties and gave good scores in these tests.

EXAMPLE 11

A composition of the present invention was prepared as follows:

A mixture of non-denatured whey protein having a whey protein concentration of 80% of total solids (WPC 80) and 2% sodium caseinate of the composition, in a protein concentration of 15% in the water phase of the composition, and 25% fish oil was prepared according to a conventional food processing method. The mixture was then transferred to a SSHE and subjected to a shear rate >600 per sec. and a temperature of 95° C. for 1-5 min. After further treatment at the same shear rate and a temperature of <75° C. in a second SSHE, an emulsion was obtained.

The emulsion provided, was tested both for physical stability and organoleptic properties and gave good scores in these tests.

EXAMPLE 12

A composition of the present invention was prepared as follows:

A mixture of non-denatured whey protein having a whey protein concentration of 80% of total solids (WPC 80) and 2% sodium caseinate of the composition, in a protein concentration of 20% in the water phase of the composition, and 20% fish oil was prepared according to a conventional food processing method. The mixture was then transferred to a SSHE and subjected to a shear rate >600 per sec. and a temperature of 85° C. for 1-5 min. After further treatment at the same shear rate and a temperature of <75° C. in a second SSHE, the composition obtained was subjected to spray drying and a powder was achieved.

The composition (emulsion) provided, was tested both for physical stability and organoleptic properties and gave good scores in these tests.

EXAMPLE 13

A composition of the present invention was prepared as follows:

A mixture of non-denatured whey protein having a whey protein concentration of 80% of total solids (WPC 80) and 2% sodium caseinate of the composition, in a protein concentration of 20% in the water phase of the composition, and 20% fish oil was prepared according to a conventional food processing method. The mixture was then transferred to a SSHE and subjected to a shear rate >600 per sec. and a temperature of 95° C. for 1-5 min. After further treatment at the same shear rate and a temperature of <75° C. in a second SSHE, the composition obtained was subjected to spray drying and a powder was achieved.

The composition (emulsion) provided, was tested both for physical stability and organoleptic properties and gave good scores in these tests.

The invention claimed is:

1. A composition consisting essentially of:
   a) a protein component from a protein source comprising a whey protein selected from the group consisting of whey protein concentrate in liquid form, whey protein concentrate in powdered form, concentrate of whey, non-concentrated whey, and mixtures of two or more of the foregoing;
   wherein the protein source comprises non-denatured whey protein in a concentration of no less than 40 wt. % of the total concentration of protein, and
   wherein the concentration of any non-whey proteins in the protein source is below 40 wt. % of the total concentration of protein in the composition, and
   wherein the denaturation percentage of the individual whey proteins in the composition is from 50% to 99%; and
   b) a lipid component not originating from the said protein component.

2. The composition of claim 1, wherein the concentration of non-denatured whey protein is no less than 50% of the total weight of the protein component.

3. The composition of claim 1, wherein the concentration of non-denatured whey protein is no less than 75% of the total weight of the protein component.

4. The composition of claim 1, wherein the concentration of non-denatured whey protein is no less than 95% of the total weight of the protein component.

5. The composition of claim 1, wherein the denaturation rate of the individual whey proteins in the composition is above 70%.

6. The composition of claim 1, wherein the source of whey protein is non-concentrated whey, whey concentrate, concentrate of whey protein from 20% to 90% of whey protein in dry matter, whey protein isolate, or a mixture thereof.

7. The composition of claim 1, wherein the source of whey protein is whey concentrate, concentrate of whey protein from 20% to 90% of whey protein in dry matter, whey protein isolate, or a mixture thereof.

8. The composition of claim 1, wherein the source of whey protein is in liquid or powdered form.

9. The composition of claim 1, wherein the said other proteins are selected from the group consisting of casein, caseinates, milk based powders, butter milk powder, plant proteins, vegetable proteins, marine proteins, egg proteins, other animal proteins, microbial proteins, hydrolysates thereof, and mixtures thereof in liquid or in powdered form.

10. The composition of claim 1, wherein the concentration of the lipid component in the composition is not more than 70% by weight of the composition.

11. The composition of claim 1, wherein the concentration of the lipid component in the composition is from about 1% to 30% by weight of the composition when present in liquid form or powdered form thereof.

12. The composition of claim 1, wherein the concentration of the lipid component in the composition is from about 10% to 25% by weight of the composition when present in liquid form or powdered form thereof.

13. The composition of claim 1, wherein the protein/lipid ratio in the composition ranges from 0.3 to 30.0.

14. The composition of claim 1, wherein the protein lipid/ratio in the composition ranges from 0.3 to 4.0.

15. The composition of claim 1, wherein the lipid component is any edible oil or fat comprising saturated, partially saturated, unsaturated fatty acids and/or derivatives thereof and/or mixtures thereof.

16. The composition of claim 1, wherein the lipid component comprises a high content of polyunsaturated fatty acids or derivatives thereof.

17. The composition of claim 1, wherein the lipid component is an oil of marine origin.

18. The composition of claim 1, wherein the said composition further comprises emulsifiers, carbohydrates, salts, antioxidants and/or flavouring agents.

* * * * *